United States Patent [19]

Moorehead

[11] Patent Number: 4,547,194
[45] Date of Patent: Oct. 15, 1985

[54] HUB ASSEMBLIES AND EXTENSIONS FOR INDWELLING CATHETER TUBES AND METHOD

[76] Inventor: Harvey R. Moorehead, 1694 E. 5685 S., Salt Lake City, Utah 84121

[21] Appl. No.: 590,310

[22] Filed: Mar. 16, 1984

[51] Int. Cl.$^4$ ............................................. A61M 25/00
[52] U.S. Cl. ...................................... 604/283; 285/24; 604/905
[58] Field of Search ............... 604/283, 280, 164, 165, 604/905; 285/24, 27

[56] References Cited

U.S. PATENT DOCUMENTS 4,354,490 10/1982 Rogers ............................ 604/283 X

FOREIGN PATENT DOCUMENTS 1125688 11/1956 France ................................. 604/283
1064445  5/1974 France ................................. 604/158
WO81/01519 11/1981 PCT Int'l Appl. .................. 604/283

Primary Examiner—Stephen C. Pellegrino
Attorney, Agent, or Firm—Lynn G. Foster

[57] ABSTRACT

Apparatus and methods are disclosed by which (a) the exposed length of an indwelling medical catheter tube is permanently extended, (b) a damaged exposed end of an indwelling catheter tube is repaired and thereby once more rendered safe and effective, and (c) a hub is easily and permanently connected to an exposed trailing end of an indwelling intravenous catheter tube or an extension thereof, all with little or no trauma to the patient.

15 Claims, 15 Drawing Figures

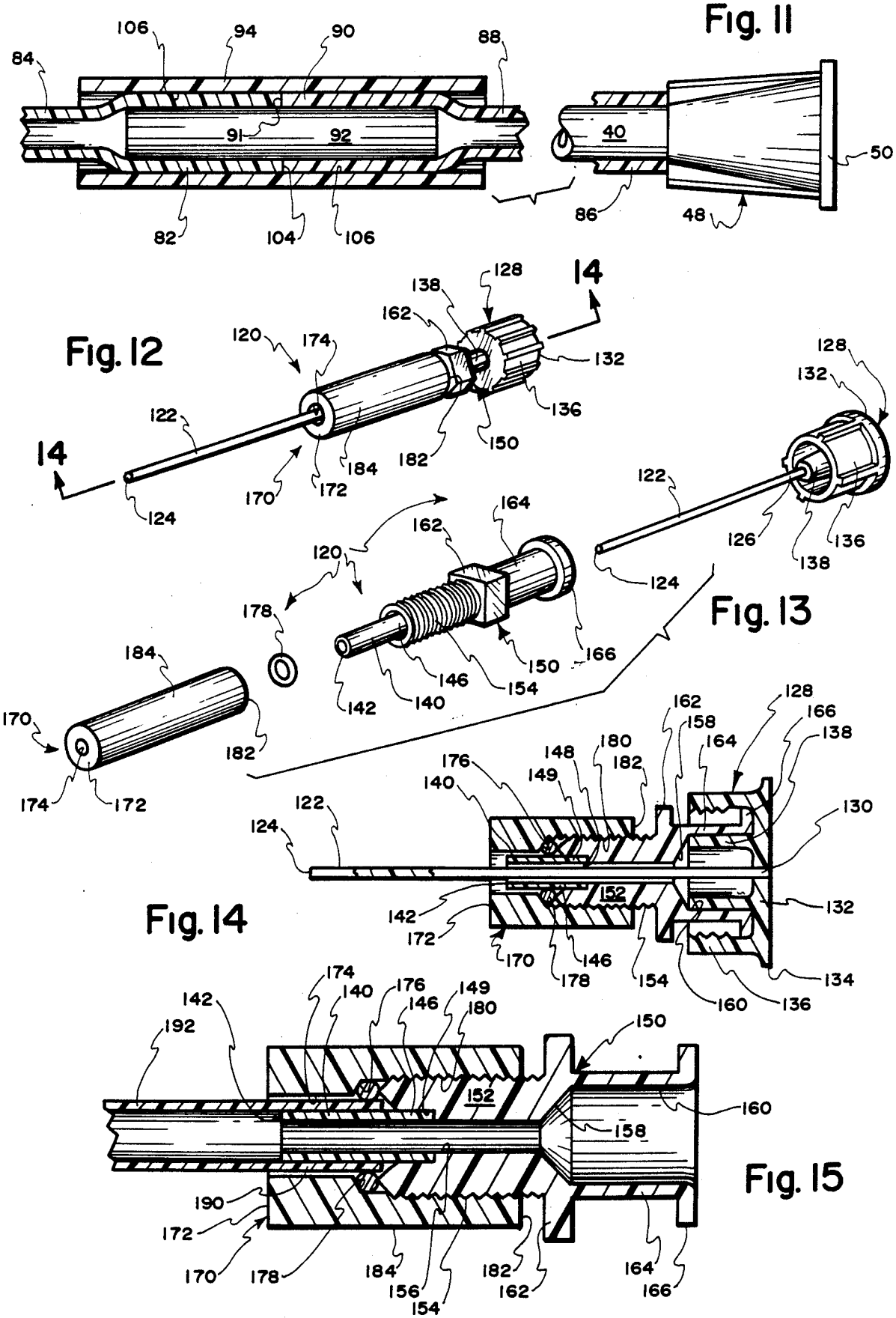

HUB ASSEMBLIES AND EXTENSIONS FOR INDWELLING CATHETER TUBES AND METHOD

FIELD OF INVENTION

The present invention relates generally to catheters and more particularly to hub assemblies and extensions for indwelling medical catheter tubes, and related methods.

PRIOR ART

No medically satisfactory apparatus or procedure has been produced heretofore for reliably extending the exposed length of an indwelling intravenous catheter tube.

Prior proposals for uniting a hub to the trailing end of an indwelling intravenous catheter tube have been basically unsatisfactory due to problems caused by misalignment, and/or the collapse and/or buckling of the catheter tube end and/or later separate between the hub and the catheter tube. Patient trauma has often been substantial since any problem associated with the indwelling catheter tube tends to be communicated directly to the patient. Hub placement on indwelling silicone rubber or other ultra pliant catheter tubes has been especially troublesome.

BRIEF SUMMARY AND OBJECTS OF THE INVENTION

In brief summary, the present invention overcomes or substantially alleviates the problems of the prior art by providing novel apparatus and unique methods by which (a) the exposed length of an indwelling intravenous catheter tube is permanently extended, and/or (b) a hub is facilely and permanently connected to the exposed trailing end of an indwelling intravenous catheter tube or an extension thereof.

With the foregoing in mind, it is a primary object of the present invention to overcome or substantially alleviate the above mentioned problems of the prior art.

It is a further dominant object to provide novel apparatus and unique methods by which the exposed length of an indwelling intravenous catheter tube is permanently extended.

It is another object of importance to provide novel apparatus and unique methods by which a damaged exposed end of an indwelling catheter can be effectively repaired with little or no trauma to the patient.

An additional object of substantial magnitude is the provision of novel apparatus and unique methods by which a hub is facilely and permanently connected to the exposed trailing end of an indwelling intravenous catheter tube or an extension thereof.

These and other objects and features of the present invention will be apparent from the detailed description with reference to the accompanying drawings.

BRIEF DESCRIPTION OF THE DRAWINGS

FIG. 11 is a side elevational view, shown partly in crosssection, similar to FIG. 10, illustrating the catheter tube extension and replacement hub fully installed;

FIG. 12 is an additional presently preferred catheter hub assembly for placement at the exposed end of an indwelling catheter tube in accordance with the present invention, illustrated in perspective;

FIG. 13 is an exploded perspective of the hub assembly of FIG. 12;

FIG. 14 is a cross-section taken along lines 14—14 of FIG. 12; and

FIG. 15 is an enlarged fragmentary cross-section similar to FIG. 14 showing the stylet and stylet hub removed and the remainder of the hub assembly installed upon the trailing end of indwelling catheter tube.

DETAILED DESCRIPTION OF THE ILLUSTRATED EMBODIMENTS

Reference is now made to the drawings, which illustrate three presently preferred embodiments in accordance with the present invention and wherein like numerals are used to designate like parts throughout.

Specific reference in detail is made at this time to FIGS. 1-8 which illustrate a hub assembly, generally designated 20, used to add a hub at the exposed end of an indwelling pliant catheter tube. The hub assembly 20 comprises a straight elongated stylet 22, preferably formed of medical grade steel or yieldable shape retaining synthetic resinous material such as polypropylene. The stylet 22 is solid and has a uniform outside diameter and extends for a substantial length along the longitudinal axis of the hub assembly 20, when in the assembled condition illustrated in FIG. 1.

Figure 3:
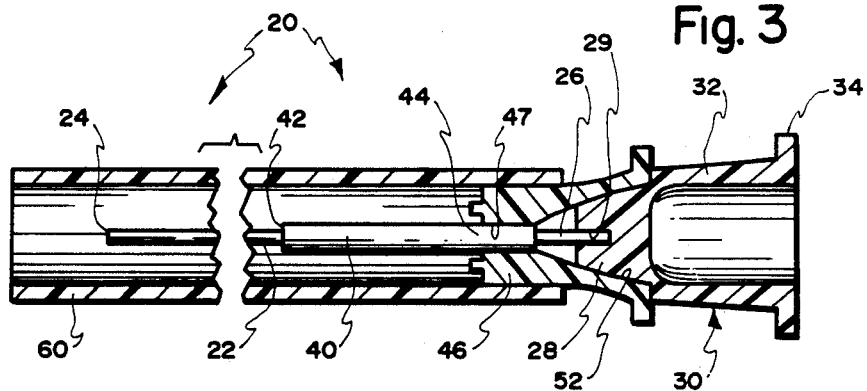
FIG. 3 is a longitudinal cross-section of the hub catheter embodiment of FIG. 1 taken along lines 3—3 of FIG. 1.
Figure 4:
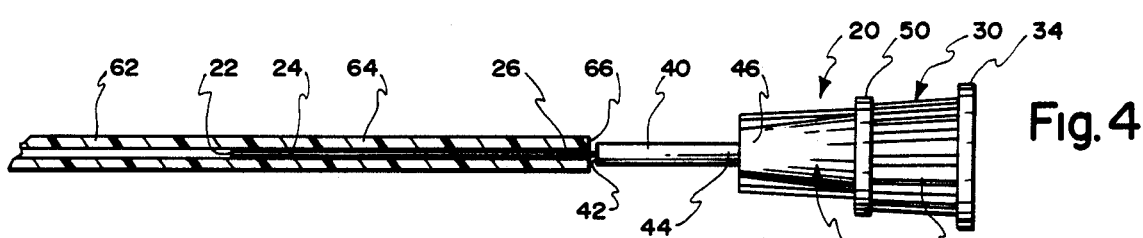
FIG. 4 is a side elevation of the hub assembly of FIG. 1, shown partly in cross-section and illustrating the initial step of insertion into an indwelling catheter tube.

The stylet 22 has a free blunt leading end 24 and a trailing end 26, which is embedded within and secured by a suitable bonding agent or the like to the forward reduced size end 28 of the stylet hub, at site 29 (FIG. 3). The stylet hub is generally designated 30. The stylet hub 30 is illustrated as having a main body 32 and a trailing flange 34, although other configurations could be used. The stylet hub 30 is preferably formed of a suitable synthetic resinous material, such as polyethylene. Thus, the stylet and stylet hub form one integral part of the hub assembly 20.

The hub assembly 20 further comprises a short hollow shaft 40 of surgical grade steel having a relatively short length and uniform inside and outside diameters. The inside diameter is slightly greater than the outside diameter of the stylet 22 and the outside diameter slightly greater than the inside diameter of the catheter tube with which the short hollow shaft 40 is to be associated, as hereinafter more fully explained.

The short hollow shaft 40 has a forward end 42 and a trailing end 44 which is anchored to a leading end 46 of a trailing hollow hub 48. Hollow hub 48 comprises a trailing flange 50, preferably with luer lock fittings to accommodate intravenous connection to parenteral fluids, hypodermic syringes and the like.

The interior of the hollow hub 48 is tapered along wall 52 (FIG. 3) so as to match and snugly receive the tapered leading portion 28 of the stylet hub 30. The hollow hub 48 is preferably formed of a suitable synthetic resinous material such as polyethylene. The connection site at 47 (FIG. 3) between the trailing end of the short hollow shaft 40 and the hollow hub 48 preferably utilizes a suitable bonding agent, such as epoxy glue, to secure the union.

Figure 1:
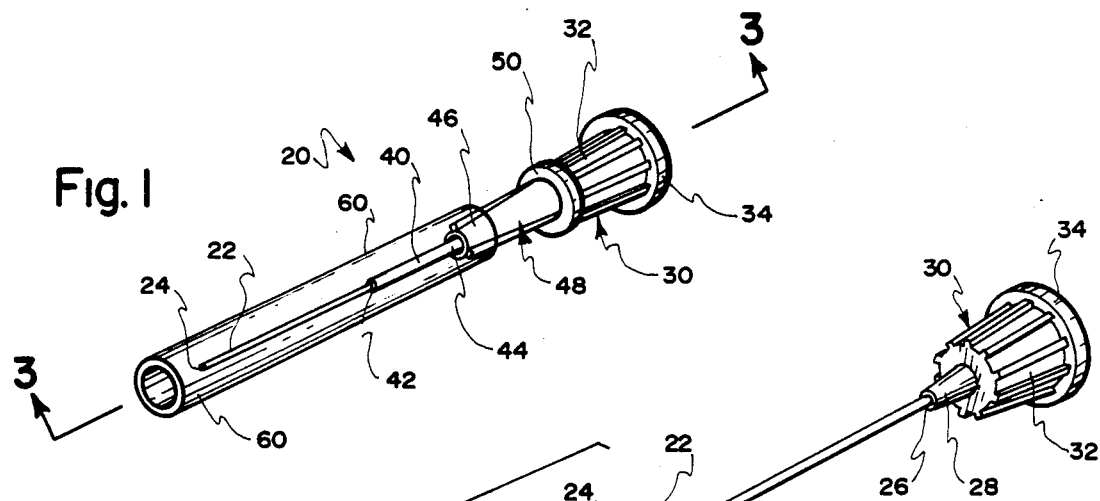
FIG. 1 is a perspective representation of one presently preferred hub assembly in accordance with the present invention for placement at the trailing end of an indwelling catheter tube.
Figure 2:
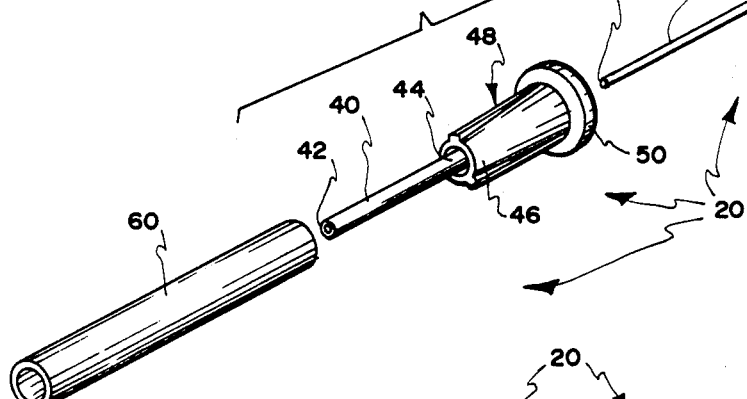
FIG. 2 is an exploded perspective representation of the catheter hub assembly of FIG. 1.

It should be apparent from inspection of FIGS. 1-3 that in the assembled position, the leading portion 28 of the hub 30 seats snugly within the hollow interior 52 of the hollow hub 48, while the stylet 22 extends through and substantially forward of the hollow short shaft 40. The hollow short shaft 40 and the stylet 22 are coaxially disposed in respect to each other as well as the longitudinal axis of the catheter assembly 20.

For the purpose of preserving sterility and preventing contamination, a hollow sheath 60 is provided, in the form of a tube formed of suitable synthetic resinous material, such as vinyl. Tubular sheath 60 is of uniform inside and outside diameter and has a length slightly greater than the length of the stylet 22. The inside diameter of tube 60 is selected so as to accommodate a press fit relation of low magnitude between the trailing end of the tube 60 and the leading portion 46 of the hollow hub 48.

Figure 5:
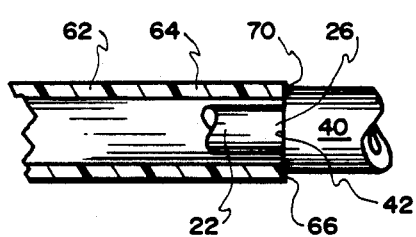
FIG. 5 is an enlarged side elevational view, shown partly in cross-section, illustrating the slightly undersized nature of the stylet, thereof and the slightly oversized nature of the hub hollow shaft thereby in comparison with the exposed end of the indwelling catheter tube.

The hub assembly 20 is used to add a hub at the exposed end of an indwelling pliant catheter tube of synthetic resinous material, silicone rubber or the like, as best shown in FIGS. 4-8. Initially, assuming the catheter tube 62 to be indwelling and its trailing end 64 to be exposed, the protective sheath 60 is removed from the hub assembly 20. Stylet 22 is manually advanced into the hollow interior (shown as having a uniform diameter) of the exposed end 64 of the catheter tube 62 until the trailing edge 66 thereof and the leading edge 42 of the hollow short shaft 40 are in substantially abutting relationship. This position is illustrated in an enlarged fashion in FIG. 5, which shows the slight interference caused at location 70 by reason of the hollow shaft 40 having a diameter slightly larger than the inside diameter of the exposed end 64 of the catheter tube 62. Thus, as illustrated in FIG. 5, the leading edge 42 of the short hollow shaft 40 initially abuts the trailing edge 66 of the catheter tube 62.

Next, concurrently or simultaneously the stylet 24 is advanced further into the hollow interior of exposed end 64 of the catheter tube 62 while the hollow short shaft 40 is manually forceably inserted into the exposed end 64 of the catheter tube 62, causing the exposed end 64 to dilate or enlarge as the short shaft 48 is advanced. The stylet or stiffener 22 surprisingly adds enormous stability to the catheter tube 62, causing the exposed end 64 to retain alignment in respect to the hub assembly 20 and preventing buckling and/or collapsing of the catheter tube 62 during the mentioned insertion of the short shaft.

Figure 6:
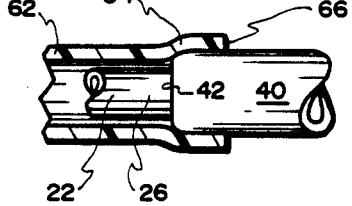
FIG. 6 is a side elevational view similar to FIG. 5, except the manner in which the exposed end of the indwelling plastic catheter is enlarged or dilated as the hollow shaft of the hub assembly is forcibly introduced, therein is shown.
Figure 7:
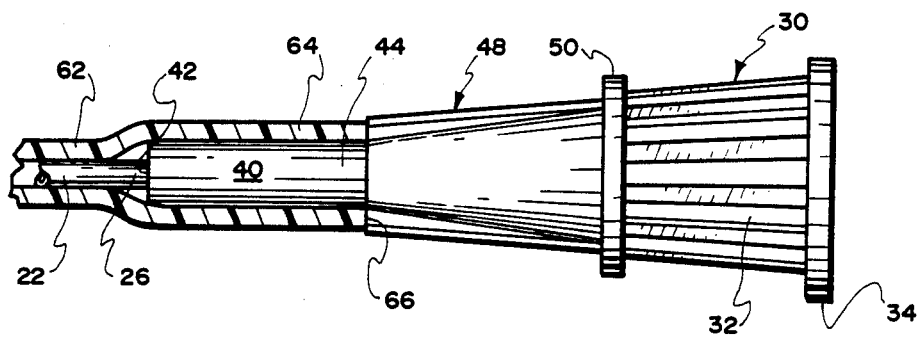
FIG. 7 is similar to FIG. 6 showing the hollow shaft of the hub assembly fully inserted, with the stylet and stylet hub remaining as part of the hub assembly.
Figure 8:
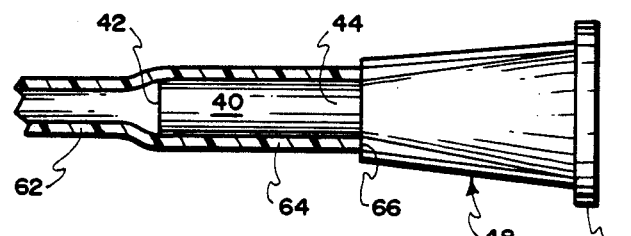
FIG. 8 is similar to FIG. 7, showing the hollow shaft of the hub assembly fully inserted with the hub thereof exposed beyond the end of the plastic catheter and the stylet and the stylet hub removed.

The initial enlargement or expansion of the exposed end 64 caused by forceable insertion of the hollow short shaft 40 therein is illustrated in FIG. 6, while FIG. 7 illustrates the short shaft fully inserted within the hollow interior of the enlarged or dilated exposed end 64 of the catheter tube. The memory of the material forming catheter tube 62 causes the exposed end 64 thereof to exert a radial compressive force against the short shaft 40 thereby holding the short shaft 40 and its associated hollow hub 48 permanently in the inserted position.

Thereafter, the stylet hub 30 is manually grasped and the stylet 22 and the hub 30 are withdrawn together, leaving the exposed trailing end 64 of the catheter tube 62 equipped with its own hub in the form of the short shaft 40 and the integral hollow hub 48 attached thereto. The flange 50 of the hub 48 may be used to receive a hypodermic syringe, or to connect to tubing which communicates intravenous fluids to the patient or may receive a suitably formed plung of a conventional nature, when it is intended that the catheter tube 62 not be used forthwith, but remain indwelling.

Figure 9:
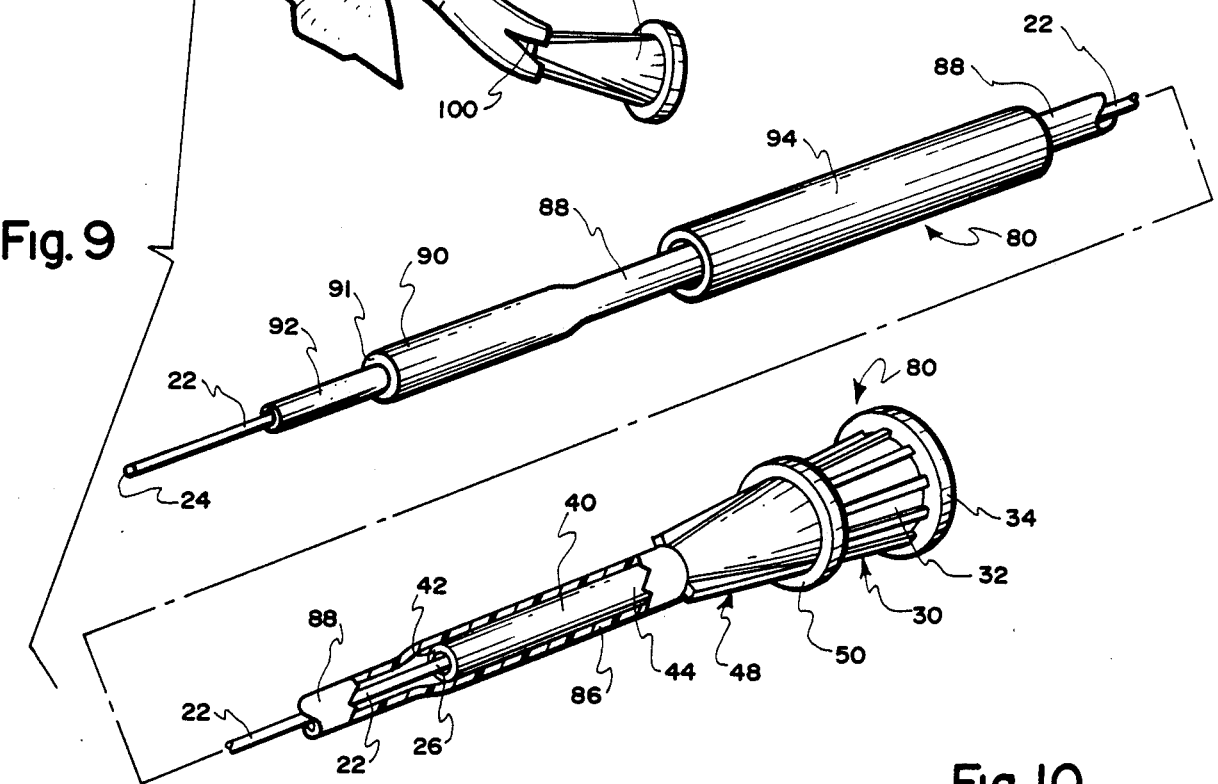
FIG. 9 is a perspective representation of a presently preferred hub repair kit assembly for replacing the hub of a damaged exposed end of an indwelling intravenous catheter tube, for extending the length of an indwelling catheter tube and providing a new hub at the end of the extension.
Figure 10:
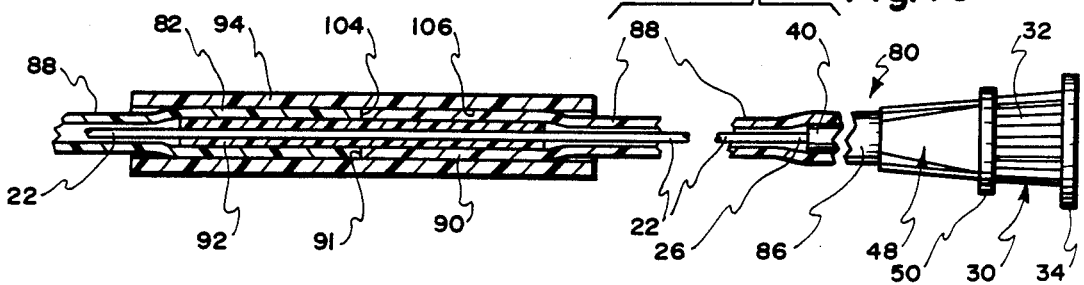
FIG. 10 is a side elevational view, shown partly in crosssection, indicating the manner in which the hub repair assembly of FIG. 9 is connected with the indwelling plastic intravenous catheter after removal of the existing damaged hub.

Reference is now made to FIGS. 9-11 which illustrate an assembly, generally designated 80, by which the length of the trailing end 82 of an intravenous catheter tube 84 is extended and a new hub provided at the end of the catheter tube extension. The apparatus 80 and the method associated therewith are particularly useful in extending the length of and providing a new hub at the trailing end of indwelling silicone rubber catheter tubes.

The assembly 80 comprises substantially the same hub assembly as described earlier in conjunction with FIGS. 1-3, except that stylet of assembly 80 has a substantially greater length. To avoid unnecessary duplicative descriptive material and to the extent the structure of assembly 80 is duplicative of the heretofore described hub assembly, identical numerals have been used in the drawings and no further description thereof will be made since such is not required for clarity.

Using a procedure of the type heretofore mentioned in conjunction with hub assembly 20, the hollow short shaft 40 of the hub assembly is placed within the trailing end 82 of a catheter tube extension 88. The catheter extension 88 is tubular and hollow having, when unstressed and at rest, a uniform inside and outside diameter. The length of the tubular extension 88 is selected to accommodate the additional length needed at the exposed end 86 of the indwelling catheter tube 84.

From the foregoing, it should be readily apparent that the short shaft 40 and the hub 48 are integrally joined to the tubular extension 88 to accommodate fluid flow of intravenous or parenteral solutions as well as the administration of drugs, such as those used in chemotherapy, where it is intended that the catheter 84 be left indwelling for a protracted period of time. In those situations where the indwelling catheter 84 is formed of silicone rubber material and, therefore, very compatible with the human body but lacking in structural integrity, the tubular extension 88 may be formed of the same material.

The tubular extension 88 is shown to be of substantial length and comprises a leading end 90 having a leading edge 91. An inside splice tube 92 is also provided. The splice tube 92 is linear, of relatively short length, has a inside diameter slightly greater than the outside diameter of the stylet 22 and an outside diameter slightly greater than the inside diameter of the tubular extension 88 and of the catheter 84.

The assembly 80 is created by sliding the relatively rigid splice tube 92 over the leading end of the stylet 22 and along the stylet 22 (with the tubular extension 88 disposed over the stylet 22 as illustrated in FIG. 9). About one-half the length of the rigid splice tube 92 is axially force fit along the stylet 22 into the leading end 90 of the tubular extension 88, causing a force fit union to exist between the leading end 90 and the splice tube 92, as illustrated in FIG. 9.

An external splice tube 94 is also provided. Splice tube 94 is straight, of relatively short length slightly greater than the length of splice tube 92 to prevent damage to the dilated ends by the internal splice tube 92, has an inside diameter slightly greater than the outside diameter of any portion of the assembly 80 forward of the hubs. Thus, the exterior splice tube 94 slidably surrounds the tubular extension 88 in the assembled condition of FIG. 9. example, through protracted use, the exposed end 82 of the indwelling catheter tube 84 has been damaged, e.g. at damage site 100 (FIG. 9) so as to render continued use thereof, in conjunction with the catheter hub 102 suspect and undesirable. Procedurally, the individual assigned to use the assembly 80 will initially cut the exposed end 82 of the catheter tube 84 at the site 104 using a sterile knife or the like. The cut should be exactly normal to the axis of the catheter tube 84. The hub 102 with damaged catheter site 100 attached thereto is discarded.

Next, the exposed leading end of the stylet 22 is inserted into the remainder of the exposed end 82 of the indwelling catheter 84, thereby properly aligning and stabilizing the end 82 against misalignment, buckling and/or collapse, bringing the transverse edge of the catheter tube 82 at site 104 into generally abutting relationship with the leading end of the interior splice tube 92.

The catheter end 82 is next manually axially displaced over the exposed remainder of the interior splice tube 92 thereby enlarging or dilating the catheter tube end 82. This process continues until the cut edge at 104 of the end 82 catheter tube is in butt relationship with the leading edge 91 of the catheter tube extension. This position is illustrated in FIG. 10, which shows that the dilated ends 82 and 90, as superimposed over the interior splice tube 92, have identical inside and outside diameters.

The force fit nature of the dilated ends 82 and 90 will serve to integrally join the catheter tube 84 to the tubular extension 88. As a further safeguard to prevent any risk whatever of separation between the catheter 84 and the tubular extension 88, the exterior splice tube 94 may be superimposed concentrically about the interior splice tube 92 so as to essentially or substantially cover the dilated ends 82 and 90. The interface between the exterior surfaces of the dilated ends 82 and 90 may be treated with a suitable adhesive at site 106 (FIG. 10) so that when the external splice tube 94 is positioned as illustrated in FIG. 10, an adhesion is created which retains the tube 94 in the position it was created.

Thereafter, by grasping the hub 30, the stylet 22 and the hub 30 are removed and the trailing end of the hollow hub 48 capped or connected to appropriate source of intravenous solution or the like, as heretofore explained. The resulting catheter extension with new trailing end hub is illustrated in FIG. 11.

Reference is now made to FIGS. 13-16, which illustrate a third presently preferred embodiment in accordance with the present invention, i.e. a hub assembly, generally designated 120. The hub assembly 120 comprises an elongated straight solid stylet 122, which has a uniform exterior diameter throughout and a substantial length. Stylet 122 has a leading blunt tip 124 and a trailing end 126 which is integrally attached to a stylet hub, generally designated 128, at site 130 (FIG. 15). Appropriate bonding agent may be used to secure the end 128 of the stylet 122 to the hub 128 at site 130.

The hub 128 has a radially directed flat back wall 132, terminating in a short radially directed flange 134 and an axially directed annular cantilevered wall 136, which serve purposes hereinafter more fully explained. The hub 126 also includes an annular cantilevered wall 138 which has an outside diameter substantially less than the inside diameter of the wall 136, also for purposes hereinafter more fully explained.

The hub assembly 120 also comprises a short hollow shaft 140, which has a relatively short length, an inside uniform diameter slightly greater than the outside uniform diameter of the stylet 122 and an outside diameter either substantially the same as or slightly smaller than the trailing end of the catheter tube on which the hub assembly is to be placed, as hereinafter more fully described. The hollow short shaft 140 has a leading edge 142 and a trailing end 146 which is anchored, at site 149 (FIG. 15) to a hollow hub, generally designated 150. A suitable bonding agent is ordinarily used at site 149 to integrally unite the trailing end 146 of the hollow shaft 140 to the hollow hub 150. It should be readily apparent that the overall length of hollow shaft 140 is substantially less than the overall length of the stylet 122 and that the stylet 122, in the illustrated configuration, is formed of rigid shape retaining though yieldable synthetic resinous material, such as polypropylene.

Hub 150 is hollow and comprises a leading end portion 152, which presents threads 154 along the exterior surface thereof and a smooth hollow central bore 156 at the interior thereof, the bore 156 having a diameter substantially the same as the inside diameter of the short shaft 140. The interior bore 156 merges with a tapered wall 158 to provide an enlarged bore 160 at the trailing end of the hollow hub 150. The leading portion 152 of the hollow hub 150 merges into a radially directed flange 162 which in turn merges into a reduced diameter tubular portion 164. The tubular portion 164 defines the enlarged trailing end opening 160 and merges integrally with a trailing flange 166, preferably equipped with luer fittings or the like to accommodate the connection to intravenous tubing, a hypodermic syringe or the like.

As can be seen from FIG. 15, the annular wall 138 of the hub 128 fits snugly within the enlarged bore 160, while the wall 136 threads upon the trailing flange 160 so that the hub 128 prevents contamination of the interior of the hub assembly 120 during storage and hub installation.

The hub assembly further comprises a generally annular sleeve, generally designated 170. The sleeve 170 has a forward blunt end 172 disposed essentially transversed to the longitudinal axis of the assembly 120 and presents a lending end bore 174 which is slightly greater in its diameter than the outside diameter of the short shaft 140. The bore 174 is enlarged at tapered wall section 176, which is sized and shaped to receive an elastomeric "O"-ring 178 between the wall 176 and the forward surface of the leading portion 182 of the hub 150.

The sleeve 170 presents an enlarged bore comprising threads 180 extending from tapered wall 176 to the trailing edge 182 of the sleeve 170. The threads at 180 and 154 are of identical type and size so that the sleeve 170 may be selectively threaded upon the hub portion 152 to manipulate the "O"-ring 178, in a fashion and for purposes hereinafter more fully explained.

In the illustrated embodiment, the cylindrical exterior 184 of the sleeve 170 is illustrated as being knurled.

The illustrated hub assembly 120 is installed by inserting the stylet 122 into the trailing end 190 of an indwelling catheter tube 192 formed of synthetic resinous material, silicone rubber or the like, and having essentially a uniform inside and outside diameter. Thus, the catheter tube end is stabilized against eccentricity in respect to hub assembly 120 during installation and buckling and collapsing of the catheter tube are also prevented.

Next, the stylet 122 is advanced farther into the hollow of the catheter tube 192 as the leading end of the short shaft is advanced into the hollow of the exposed end 190 of the catheter tube 192. Preferably, the outside diameter of the short shaft 140 as slightly less than the inside diameter of the catheter tube 192 when at rest as shown, allowing the exposed end 190 of the catheter end 192 to slide unrestrained upon the short shaft.

Once the short shaft is alignedly and fully inserted into the end 190 of the catheter tube, the sleeve 170 is at this point in time is manually rotated in a rearwardly direction along threads 154 of hollow hub portion 152 until such time as the "O"-ring 178 has been collapsed or compressed from its round cross sectional configuration to an eliptical configuration thereby causing the "O"-ring 178 to apply substantial pressure to the exterior surface of the exposed end 190 of the catheter tube 192 thereby securing the connection between the hub assembly 120 and the exposed end of the catheter tube. The degree of exterior catheter pressure asserted by the "O"-ring is controlled by the amount of sleeve rotation. It is to be understood that the initial inside diameter of the "O"-ring 170 is selected to be slightly greater than the outside diameter of the catheter tube end 190 and that the mentioned sleeve rotation in effect selectively reduces the inside diameter of the "O"-ring.

Once the stylet 120 and the stylet hub 128 are manually removed, the hollow hub 150 may be capped, connected to intravenous tubing, connected to a hypodermic syringe or the like, to service the needs on a long-term basis of the indwelling catheter tube 192.

The invention may be embodied in other specific forms without departing from the spirit or essential characteristics thereof. The present embodiments are therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by the United States Letters Patent is:

1. A method of integrally adding a hub at the trailing end of an indwelling hollow pliant catheter tube comprising the steps of:

providing, at a point in time after the proximal end of a catheter tube has become indwelling within a patient so that the distal end of catheter tube is exposed outside the patient, a separate structure for insitu formation of a hub on the distal end of catheter tube;

causing the separate structure to include a short rigid essentially non compressible hollow shaft, with a trailing hollow hub attached thereto, concentrically telescopically superimposed over a trailing portion of an elongated flexible anti-buckling hub stylet, the stylet having a length substantially greater than the length of the hollow shaft and an outside diameter less than the inside diameter of the catheter tube, and the hollow shaft having an outside diameter slightly greater than the inside diameter of the catheter tube;

advancing the elongated flexible stylet into the hollow interior of the exposed end of the indwelling pliant catheter tube in essentially concentric fashion, the stylet (a) preventing the catheter tube from collapsing and buckling due to applied external forces, (b) causing an initial substantial concentricity between the stylet and the catheter tube, and (c) bringing the leading edge of the hollow shaft into essentially aligned, contiguously abutting relationship with the exposed distal end edge of the indwelling catheter tube;

advancing the stylet further into the indwelling catheter tube and simultaneously forcibly alignedly advancing the hollow shaft into the exposed end and along the interior of the catheter tube without material trauma to the patient thereby dilating the distal end of the indwelling catheter tube counter to the forces comprising the memory of the material from which the catheter tube is made, while preventing the collapsing and buckling of the catheter tube and retaining said substantial concentricity and essential alignment notwithstanding the axial advancement force and the radial enlargement force imposed upon the distal end of indwelling catheter tube;

terminating said simultaneous advancement when substantially the full length of the hollow shaft has been force fit within the dilated exposed distal end of the catheter tube;

retaining the hub in the installed position by reason of the compressive memory force of the dilated distal end of the catheter tube upon the short rigid shaft;

removing the stylet from the hollow shaft and the hub.

2. A method according to claim 1, wherein the anti-buckling stylet is formed of resilient synthetic resinous material with memory.

3. A method according to claim 1, wherein the catheter tube is formed of silicone rubber material.

4. A method according to claim 1 wherein the shaft is formed of medical grade steel and the hub is formed of rigid synthetic resinous material.

5. A separate hub assembly for placing a hub thereof insitu at the exposed distal end of an indwelling axially unstable catheter tube of synthetic resinous material after insertion of the proximal end of the catheter tube into a patient without material trauma to the patient comprising:

an elongated thin resilient flexible essentially straight catheter tube stabilizing hub stylet for manual introduction into the exposed distal end of the indwelling catheter tube having an outside diameter less than the inside diameter of the distal end of the catheter tube;

a rigid hollow hub shaft concentrically and coaxially surrounding a trailing portion of the stylet for manual introduction, without use of a tool, into and expansion of the exposed end of the indwelling catheter tube after introduction of the stylet, the hub shaft having an axial length substantially less than the axial length of hub stylet and having an outside diameter greater than the inside diameter of a catheter tube;

a hollow hub integrally connected to the trailing end of the hub shaft to accommodate fluid flow along the hollow interior of the hub shaft and along the catheter tube after forcible insertion of the hub shaft into the distal end of the catheter tube;

a stylet hub integrally connected to the trailing end of the stylet and disposed adjacent but beyond the trailing end of the hub shaft hub by which the stylet is withdrawn from the hub shaft;

whereby the stylet stabilizes the exposed distal end of the catheter tube against collapse and buckling as the hub shaft is manually axially force fit without use of a tool into the exposed distal end of the catheter tube to expand the diameter thereof counter to the memory of the catheter tube material after which the hub shaft is firmly retained within the exposed distal end of the catheter tube by reason of compressive force of said memory and the stylet is withdrawn from the hub shaft and the hub shaft hub through the hollow of the hub shaft by manual manipulation of the stylet hub.

6. A method of extending the length of the exposed end of an indwelling intravenous catheter tube, and providing a hub at the end of the extended catheter tube, comprising the steps of:

providing an elongated straight resilient stylet having a substantial length and an outside diameter less than the inside diameter of an existing indwelling catheter tube, the stylet having a stylet hub at the trailing end thereof;

providing a hollow catheter tube extension, having inside and outside diameters substantially identical with the inside and outside diameters of the exposed end of the indwelling catheter tube, respectively, the catheter tube extension being superimposed over the length of the stylet, exclusive of a substantial portion of the leading end of the stylet, the catheter tube extension having a hub immediately forward of the stylet hub;

providing a stiff splice tube, some of the length thereof being telescopically disposed within the leading end of the catheter tube extension and the remaining length thereof projecting forward of the leading end of the catheter tube extension to a location an appreciable distance behind the forward end of the stylet, the outside diameter of the splice tube being slightly greater than the inside diameter of the catheter tube;

inserting the forward end of the stylet into the exposed end of the indwelling catheter tube until the transverse edge of the exposed end of the indwelling catheter tube and the forward edge of the splice tube substantially abutt;

concurrently advancing the stylet further into the indwelling catheter tube and the leading end of the stiff splice tube forcibly into the trailing end of and along the interior of the indwelling catheter tube thereby dilating the circumscribing catheter tube while retaining a substantial concentricity between the stylet and the splice tube on the one hand and the exposed end of the indwelling catheter tube on the other hand;

terminating the concentrically advancing step when the trailing edge of the indwelling catheter tube extension and the catheter tube are generally in abutting aligned relationship;

removing the stylet and the stylet hub from association with the catheter tube extension, the exposed end of the indwelling catheter tube and the hub at the end of the indwelling catheter tube extension.

7. A method according to claim 6 further comprising the step of placing an external splice tube having an inside diameter on the order of the same diameter as the outside diameter of the catheter tube and the catheter tube extension so as to span the abutting interface between the catheter extension and the catheter tube coaxially and coextensively with said splice tube and securing said external splice sleeve in said position.

8. An assembly for extending the length of the exposed end of an indwelling intravenous catheter tube, and providing a hub at the end of the extended catheter tube, the assembly comprising:

an elongated straight resilient stylet having a substantial length and an outside diameter less than the inside diameter of an existing indwelling catheter tube;

a stylet hub located at the trailing end thereof;

a hollow catheter tube extension, having inside and outside diameters substantially identical with the inside and outside diameters of the exposed end of the indwelling catheter tube, respectively, the catheter tube extension being superimposed over the length of the stylet exclusive of a substantial portion of the leading end of the stylet;

a hollow hub attached to the trailing end of the catheter tube extension and disposed immediately forward of the stylet hub;

a stiff splice tube, some of the length thereof being telescopically disposed within the leading end of the catheter tube extension and remaining length thereof projecting forward of the leading end of the catheter tube extension to a location an appreciable distance behind the forward end of the stylet, the outside diameter of the splice tube being slightly greater than the inside diameter of the catheter tube;

thereby accommodating insertion of the forward end of the stylet into the exposed end of the indwelling catheter tube until the transverse edge of the exposed end of the indwelling catheter tube and the forward edge of the splice tube substantially abutt and thereafter accommodating concurrent advancement of the stylet further into the indwelling catheter tube and the leading end of the stiff splice tube forcibly into the trailing end of an along the interior of the indwelling catheter tube thereby dilating the circumscribing catheter tube while a substantial concentricity is retained between the stylet and the splice tube on the one hand and the indwelling catheter tube on the other hand until the trailing edges of the indwelling catheter tube extension and the catheter tube are generally in abutting aligned relationship allowing removal of the stylet and the stylet hub from association with the catheter tube extension, the exposed end of the indwelling catheter tube and the hub at the end of the indwelling catheter tube extension and use of the catheter tube and catheter tube extension for fluid flow.

9. A method for extending the length of the exposed end of an indwelling intravenous catheter tube, comprising the steps of:
providing an elongated straight resilient stylet having a substantial length and an outside diameter less than the inside diameter of an existing indwelling catheter tube;
providing a hollow catheter tube extension, having inside and outside diameters substantially identical with the inside and outside diameters of the exposed end of the indwelling catheter tube, respectively, the catheter tube extension being superimposed over the length of the stylet exclusive of a substantial portion of the leading end of the stylet;
providing an internal stiff splice tube, some of the length thereof being telescopically disposed within the leading end of the catheter tube extension and the remaining length thereof projecting forward of the leading end of the catheter tube extension to a location an appreciable distance behind the forward end of the stylet, the outside diameter of the splice tube being slightly greater than the inside diameter of the catheter tube;
inserting the forward end of the stylet into the exposed end of the indwelling catheter tube until the transverse edge of the exposed end of the indwelling catheter tube and the forward edge of the splice tube substantially abutt;
concurrently advancing the stylet further into the indwelling catheter tube and the leading end of the stiff splice tube forcibly into the trailing end of and along the interior of the indwelling catheter tube thereby progressively dilating the circumscribing catheter tube while retaining a substantial concentricity between the stylet and the splice tube on the one hand and the exposed end of the indwelling catheter tube on the other hand;
terminating the concentrically advancing step when the trailedges of the indwelling catheter tube extension and the catheter tube are generally in abutting aligned relationship.

10. A method according to claim 9 further comprising the step of placing an external splice tube having an inside diameter on the order of the same diameter as the outside diameter of the catheter tube and the catheter tube extension so as to exteriorly span the abutting interface between the catheter extension and the catheter tube substantially coaxially and coextensively with said splice tube and securing said external splice sleeve in said position.

11. A method according to claim 9 further comprising the step of cutting a hub to be discarded from the exposed end of the catheter tube prior to the inserting step.

12. A method of integrally adding a hub at the trailing end of an indwelling hollow pliant catheter tube comprising the steps of:
causing a short hollow hub assembly shaft, with a trailing hollow hub attached thereto, to be concentrically telescopically superimposed over a trailing portion of an elongated flexible antibuckling hub assembly stylet, the stylet having a length substantially greater than the length of the hollow hub assembly shaft and an outside diameter less than the inside diameter of the catheter tube;
advancing the elongated flexible stylet into the hollow interior of the exposed end of the indwelling pliant catheter tube in essentially concentric fashion, the stylet preventing the catheter tube from collapsing and buckling due to applied external forces, causing an initial substantial concentricity between the stylet and the catheter tube, and bringing the leading edge of the hollow hub shaft into the same proximity as the exposed end edge of the indwelling catheter tube;
advancing the stylet further into the catheter tube and simultaneously advancing the hollow shaft into the exposed end and along the interior of the catheter tube with no more than a small amount of dilation while preventing the collapsing and buckling of the catheter tube and retaining said substantial concentricity and essential aligment;
terminating said simultaneous advancement when substantially the full length of the hollow hub shaft is disposed within the exposed end of the catheter tube;
applying continuous external radial pressure to the superimposed exposed end of the catheter tube and the hub assembly shaft;
removing the stylet from the hollow hub shaft and the hub.

13. A method according to claim 12 wherein the pressure of the applying step is selectively variable, being applied by a "O" ring the inside diameter of which is varied by the extent of engagement of male and female threaded members comprising the hub assembly.

14. A hub assembly for placing a hub thereof at the exposed end of an indwelling catheter tube after catheter tube insertion comprising;
an elongated thin resilient flexible essentially straight hub assembly stylet having an outside diameter less than the inside diameter of the catheter tube;
a rigid hub assembly shaft concentrically and coaxially surrounding a trailing portion of the stylet, the hub assembly shaft having an axial length substantially less than the axial length of hub assembly stylet;
a hollow hub integrally connected to the trailing end of the hub assembly shaft adapted to accommodate fluid flow along the hollow interior of the hub assembly shaft and along the catheter tube;
another hub integrally connected to the trailing end of the stylet and disposed adjacent but behind the trailing end of the hollow hub;
whereby the stylet stabilizes the trailing end of the catheter tube against collapse and buckling as the hub assembly shaft is displaced into the exposed end of the catheter tube after which the stylet may be withdrawn from the hub shaft and the hollow hub by manual manipulation of the other hub;
the hub assembly further comprising means by which external force is releasibly and adjustably applied to at least part of the exposed end of the catheter tube in which the hub assembly shaft coextends.

15. A hub assembly for placing a hub thereof at the exposed end of an indwelling catheter tube after catheter tube insertion comprising:

an elongated thin resilient flexible essentially straight hub assembly sytlet having an outside diameter less than the inside diameter of the catheter tube;

a rigid hub assembly shaft concentrically and coaxially surrounding a trailing portion of the stylet, the hub assembly shaft having an axial length substantially less than the axial length of hub assembly stylet;

a hollow hub integrally connected to the trailing end of the hub assembly shaft adapted to accommodate fluid flow along the hollow interior of the hub assembly shaft and along the catheter tube;

another hub integrally connected to the trailing end of the stylet and disposed adjacent but behind the trailing end of the hollow hub;

whereby the stylet stabilized the trailing end of the catheter tube against collapse and buckling as the hub assembly shaft is displaced into the exposed end of the catheter tube after which the stylet may be withdrawn from the hub shaft and the hollow hub by manual manipulation of the other hub;

the hub assembly further comrpising means by which external force is applied to at least part of the exposed end of the catheter tube in which the hub assembly shaft coextends the last mentioned means comprising an "O"-ring and the pressure applied by the "O"-ring to the end of the catheter tube, in which the hub assembly shaft is disposed, is variable depending on the extent of engagement of male and female threaded members comprising the hub assembly.

* * * * *